United States Patent
Fitzgerald et al.

(10) Patent No.: US 11,383,216 B2
(45) Date of Patent: Jul. 12, 2022

(54) RELATING TO SUBSTRATES FOR THE ATTACHMENT OF MOLECULES

(71) Applicants: Randox Laboratories Ltd., Northern Ireland (GB); Randox Teoranta, Donegal (IE)

(72) Inventors: Peter Fitzgerald, Northern Ireland (GB); John Lamont, Northern Ireland (GB); Ivan McConnell, Northern Ireland (GB); Elouard Benchikh, Northern Ireland (GB); Deepesh Upadhyay, Northern Ireland (GB); Ciaran Richardson, Donegal (IE)

(73) Assignees: Randox Laboratories, Ltd., Crumlin (GB); Randox Teoranta, Donegal (IE)

( * ) Notice: Subject to any disclaimer, the term of this patent is extended or adjusted under 35 U.S.C. 154(b) by 292 days.

(21) Appl. No.: 16/424,330

(22) Filed: May 28, 2019

(65) Prior Publication Data
US 2019/0344240 A1 Nov. 14, 2019

Related U.S. Application Data

(63) Continuation of application No. 16/388,527, filed on Apr. 18, 2019, which is a continuation of application
(Continued)

(30) Foreign Application Priority Data
Nov. 18, 2015 (GB) ..................................... 1520341

(51) Int. Cl.
*B01J 19/00* (2006.01)
*C09D 11/102* (2014.01)
(Continued)

(52) U.S. Cl.
CPC .......... *B01J 19/0046* (2013.01); *C09D 11/03* (2013.01); *C09D 11/102* (2013.01); *C12M 1/00* (2013.01);
(Continued)

(58) Field of Classification Search
CPC ................................................ B01L 2300/161
(Continued)

(56) References Cited

U.S. PATENT DOCUMENTS

| 2003/0003474 A1* | 1/2003 | Tanner ............... B01J 20/28033 |
| | | 427/2.11 |
| 2003/0148401 A1* | 8/2003 | Agrawal ............. B81C 1/00206 |
| | | 506/9 |

(Continued)

FOREIGN PATENT DOCUMENTS

| CN | 103233274 B | 12/2014 |
| EP | 0 874 242 A1 | 10/1998 |

(Continued)

OTHER PUBLICATIONS

Romanov et al., "A critical comparison of protein microarray fabrication technologies", Analyst, 2014, 139, 1303.
(Continued)

*Primary Examiner* — Ian A Rummel
(74) *Attorney, Agent, or Firm* — Gavrilovich, Dodd & Lindsey LLP

(57) ABSTRACT

A substrate comprising a coating of a masking material, and a plurality of discrete reaction zones onto which one or more binding agents are intended to be attached, wherein said zones are uncoated areas on the substrate.

22 Claims, 5 Drawing Sheets

Related U.S. Application Data

No. 15/983,484, filed on May 18, 2018, now Pat. No. 10,279,332, which is a continuation of application No. PCT/GB2016/053608, filed on Nov. 18, 2016.

(51) Int. Cl.
  *C09D 11/03* (2014.01)
  *G01N 33/543* (2006.01)
  *C12M 1/00* (2006.01)

(52) U.S. Cl.
  CPC ............... *G01N 33/54393* (2013.01); *B01J 2219/00608* (2013.01); *B01J 2219/00637* (2013.01)

(58) Field of Classification Search
  USPC ........................................ 428/195.1
  See application file for complete search history.

(56) References Cited

U.S. PATENT DOCUMENTS

| | | |
|---|---|---|
| 2003/0219816 A1 | 11/2003 | Solomon et al. |
| 2004/0146920 A1 | 7/2004 | Lee |
| 2004/0213986 A1* | 10/2004 | Kim ............... G01N 33/54393 428/315.7 |
| 2012/0035081 A1 | 2/2012 | Lin |

FOREIGN PATENT DOCUMENTS

| | | |
|---|---|---|
| EP | 0 895 083 A2 | 2/1999 |
| JP | 2002065274 A | 3/2002 |
| JP | 2003014760 A | 1/2003 |
| WO | 02/092833 A2 | 11/2002 |
| WO | 2006/023324 A1 | 3/2006 |
| WO | 2013/063382 A2 | 5/2013 |
| WO | 2013/130674 A1 | 9/2013 |

OTHER PUBLICATIONS

Cretich et al., "Protein microarray technology: how far off is routine diagnostics?" The Analyst, vol. 139, No. 3, pp. 528-542, Jan. 1, 2014.

Petersson et al., "Generation of miniaturized planar recombinant antibody arrays using a microcantilever-based printer," Nanotechnology, vol. 25, No. 27, p. 275104, Jun. 24, 2014.

van der Kooij, M., International Search Report and Written Opinion, PCT/GB2016/053608, European Patent Office, Feb. 27, 2017.

* cited by examiner

RELATING TO SUBSTRATES FOR THE ATTACHMENT OF MOLECULES

CROSS REFERENCE TO RELATED APPLICATIONS

This application is a continuation of U.S. patent application Ser. No. 16/388,527, filed Apr. 18, 2019, which is a continuation U.S. patent application Ser. No. 15/983,484, filed May 18, 2018, which is a continuation of PCT/GB2016/053608, filed Nov. 18, 2016, which application claims priority under 35 U.S.C. § 119 to Great Britain Application No. 1520341.7, filed Nov. 18, 2015, the disclosures of which are incorporated herein in their entirety for all purposes.

FIELD OF THE INVENTION

The present invention relates to improvements to substrates for the attachment of binding agents. In particular, the present invention is directed to an improved micro-array substrate. In another aspect there is provided an improved composition for use in coating a substrate for the attachment of binding agents and in particular for use in coating a substrate for a micro-array. In a further aspect of the invention there is provided an improved method for analysing a micro-array.

BACKGROUND OF THE INVENTION

Use of fabricated arrays of molecules in the detection and characterisation of analytes is well known. For example, fabricated arrays of polynucleotides are used widely in DNA sequencing procedures and in hybridisation studies for the detection of genetic variations in a patient. Immunoassays are also well known for detecting analytes, such as specific proteins or other binding agents, through their properties as antigens or antibodies.

Micro-array substrates typically comprise a supporting material comprising a plurality of reaction zones located in spatially distinct areas on the substrate. The provision of multiple reaction zones allows simultaneous testing of multiple analytes or biomarkers in a sample. Micro-arrays are important laboratory tools, not only allowing a more comprehensive analysis of a patient's condition but also saving the time and cost associated with laboratory tests. Typically, micro-arrays are manufactured by depositing or "spotting" molecules or molecular fragments onto the substrate to form an array of reaction zones. In order to obtain an acceptable quality of data, the spotting should be uniform so that the spots are of the same size and shape. However, the data obtained from currently available micro-arrays still has scope for improved accuracy and precision to be more effective in both research and clinical settings. Relatively little has been done to address this problem.

It would therefore be beneficial to provide a substrate that gives high quality data.

SUMMARY OF THE INVENTION

In accordance with an aspect of the invention, there is provided a substrate comprising a coating of a masking material, and a plurality of discrete reaction zones onto which one or more binding agents are intended to be covalently attached, wherein said zones are uncoated areas on the substrate.

It has surprisingly been found that the coated substrate of the present invention provides improved detection sensitivity and image quality, especially when using digital sensors. The coated areas of the substrate reduce non-specific binding and the cross-linking of the spots and so background noise is reduced resulting in an enhanced signal-to-noise ratio. This means that the signal obtained is proportional to the extent of the "true" binding that has occurred between the sample and the targets on the substrate. Increased spatial resolution is also achieved.

Furthermore, use of a coated substrate according to the present invention allows improved accuracy of deposition of binding agents. Internal calibration marks can be fabricated on the substrate to enable accurate identification of discrete reaction zones for accurate biomolecule deposition within the zones.

DESCRIPTION OF THE DRAWINGS

FIG. 2a shows an image of the substrate 1 without predefined discrete reaction zones. FIG. 2b shows an image of a substrate 1 comprising a coating of masking material 2, having predefined non-silicon discrete reaction zones.

FIG. 3a shows an image of the substrate 1 without predefined discrete reaction zones. FIG. 3b shows an image using a substrate 1 comprising a coating of masking material 2 and with predefined discrete reaction zones.

FIGS. 2 and 3 show microarrays according to the present invention that have low background noise signal and antiblooming properties.

DETAILED DESCRIPTION OF THE INVENTION

Figure 1:
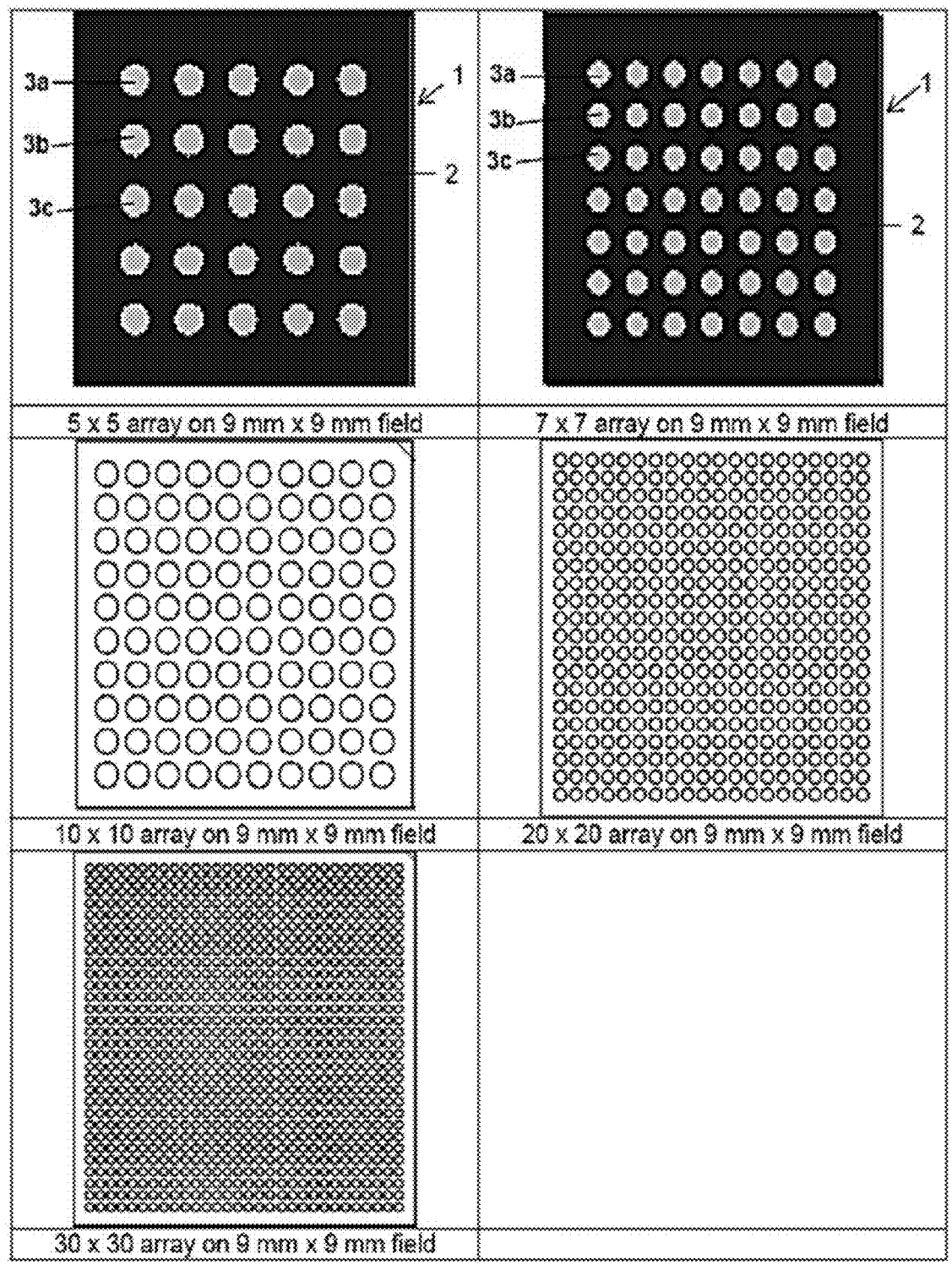
FIG. 1 shows schematic illustrations of microarrays having low to high density array format on a 9 mm×9 mm field. Each microarray in FIG. 1 comprises a substrate 1, a coating of a masking material 2 and uncoated discrete reaction zones 3a, 3b, 3c.

The present invention provides a substrate comprising a coating of a masking material, and a plurality of discrete reaction zones onto which one or more binding agents are intended to be attached, wherein said zones are uncoated areas on the substrate.

The substrate is preferably a 5×5, 7×7, 10×10, 20×20 or 30×30 micro-array substrate. The term micro-array is not intended to be limited to the detection of any particular molecule and encompasses all types of array including RNA, DNA, protein arrays, and any other arrays for the detection of biomolecules or biomolecular fragments. Preferably, the binding agents to be attached to the microarray are proteins. More preferably, the binding agents to be attached to the micro-array are antibodies. Most preferably, the substrate is a protein microarray substrate.

The substrate itself may comprise any suitable material known to the skilled person. Preferably the substrate comprises silicon, metal oxides, ceramic, glass or plastic. More preferably, the substrate is a ceramic substrate. More preferably the ceramic is aluminium oxide based. Most preferably the substrate is a white ceramic substrate. This gives the most contrast between the substrate and the coating of a masking material that is applied to the substrate.

A ceramic substrate may be manufactured to provide a range of grain sizes (1 to 30 μm). The preferred particle size of the ceramic substrate used in this invention is less than 20 μm, preferably less than 10 μm. The reduced particle size imparts much improved surface uniformity which in turn provides enhanced performance of biological assays.

The preferred ceramic material consists of about 96% alumina ($Al_2O_3$) with a particle size in the range of 4-8 μm. The material is vacuum-tight, and has a surface topography of 0.6 to 0.8 μm when ground. The surface uniformity can be improved by a polishing process, to yield a surface with variation of 0.4-0.5 μm. A further improvement is achieved by lapping and polishing, to yield a surface with a variability of 0.05-0.1 μm.

Preferably the coating is a non-silicon containing coating and preferably lacks elemental silicon or a compound incorporating silicon. Silicon-containing coatings are known in the prior art e.g. silicone. However the inventors have found that when using such coatings, silicon can contaminate the discrete reaction zones, which has a detrimental effect on attachment of binding agent.

Any suitable non-silicon masking or coating may be used. Preferably the coating comprises one or more resins selected from the list of acrylics, alkyds, epoxides, hydrocarbons, phenolics or fluoropolymers such as a polytetrafluoroethylene (PTFE). The coating may also contain any suitable ink solvents and/or ink additives. Particularly preferred ink solvents include cyclohexanone, butoxyethanol and aromatic distillates. Particularly preferred ink additives include carbon black (black pigment), mineral oil (wetting agent), petroleum distillate, dibutyl phthalate (plasticiser), salts of cobalt, manganese or zirconium (drying agent), aluminium and titanium chelator (chelating agent), antioxidants, surfactants and defoamers.

Preferably the coating (masking material) comprises epoxy and acrylic resin, a pigment and a structuring agent. One pigment may be present or multiple pigments may be used. Epoxy and acrylic resin are used to increase ink viscosity, rheological properties and adhesion to the substrate. The pigment imparts a dark colour, preferably a black colour, and hence imparts optical opacity to the ink. The structuring agent provides hydrophilic/hydrophobic properties to the surface of the substrate and also help adhesion to the substrate.

Preferably the pigment is present in an amount of 1 to 15% w/w of the masking composition (masking material); the epoxy resin is present in an amount of 10 to 60% w/w, the acrylic resin is present in an amount of 1 to 20% w/w, and the structuring agent is present in an amount of 10 to 60% w/w.

More preferably, the pigment, preferably black pigment, is present in an amount of 1 to 8% w/w of the masking composition; the epoxy resin is present in an amount of 15 to 50% w/w of the masking composition, the acrylic resin is present in an amount of 2 to 15% w/w of the masking composition, and the structuring agent is present in an amount of 15-50% w/w of the masking composition.

Most preferably, the pigment, preferably black pigment, is present in an amount of 5% w/w of the masking composition; the epoxy resin is present in an amount of 30% w/w of the masking composition, the acrylic resin is present in an amount of 10% w/w of the masking composition, and the structuring agent is present in an amount of 20% w/w of the masking composition.

In a preferred embodiment, carbon black pigment is used in the masking material, preferably Elftex 285. Preferably the acrylic resin is B-67. Preferably the structuring agent is a PTFE wax, such as CERAFLOUR® 965. Preferably, the masking material comprises an epoxy resin, preferably Epikote 1004.

Most preferably, the pigment is Elftex 285, the acrylic resin is B-67, the epoxy resin is Epikote 1004 and the structuring agent is CERAFLOUR® 965.

The coating (masking material) may further comprise one or more agents selected from the list of solvents, such as ethanol, propanol, xylene, diglycol, butyl ether; dispersing agents; pigment wetting agents; levelling agents; pigment wetting agents and/or crosslinking agents.

Preferably, the coating has a contact angle of 20-175°, more preferably 20-170° more preferably 90-120°, even more preferably about 110°. The measurement is taken using the following protocol: The contact angle is measured using a KSV CAM200 contact angle meter equipped with automated dispenser controlled using stepper motor, LED source and CCD camera. The contact angle meter is connected to a software tool for dispense controller, image grabbing and image analysis. A droplet of deionised water of 3.5 μl is dispensed on the substrate at a predefined location and the image is captured using a CCD camera. Image analysis is performed using software to estimate the contact angle of the water droplet.

Preferably, the thickness of the coating applied to the substrate is 1-100 μm thick, preferably, 2-50 μm thick. This creates a discrete reaction zone that is a well having a depth of 1-100 μm, preferably 2-50 μm, respectively. Most preferably the thickness of coating is 3 to 20 μm thick μm and the resulting depth of the well is 3 to 20 μm in depth.

The walls of the discrete reaction zones, or wells, are formed by the surrounding coating. When a buffer solution containing antibody or other biomolecule is spotted onto the discrete reaction zones, the antibody, or biomolecule, is immobilised on the activated surface. The walls of the each discrete reaction zone absorb scattering light leading to improved data readings.

Preferably, the substrate comprises a hydrophobic mask coating, and a plurality of discrete reaction zones onto which one or more binding agents are intended to be attached, wherein said zones are uncoated areas on the substrate.

Preferably, the coating is darker than the substrate. This will provide contrast between the discrete reaction zones and the surrounding coated area. More preferably, the substrate is white and the coating is any colour ranging from off-white to black. Any colour other than white will provide contrast between the discrete reaction zones and the surrounding coated area. The contrast between the discrete reaction zones and the surrounding area of coated substrate gives better spatial resolution and allows accurate data even with a high density of discrete reaction zones. The term "masking" material herein means any material used to coat the substrate, preferably having a colour darker than the substrate.

Preferably the masking material has a colour ranging from off-white to black. More preferably, the masking material has a matt finish.

Figure 5:
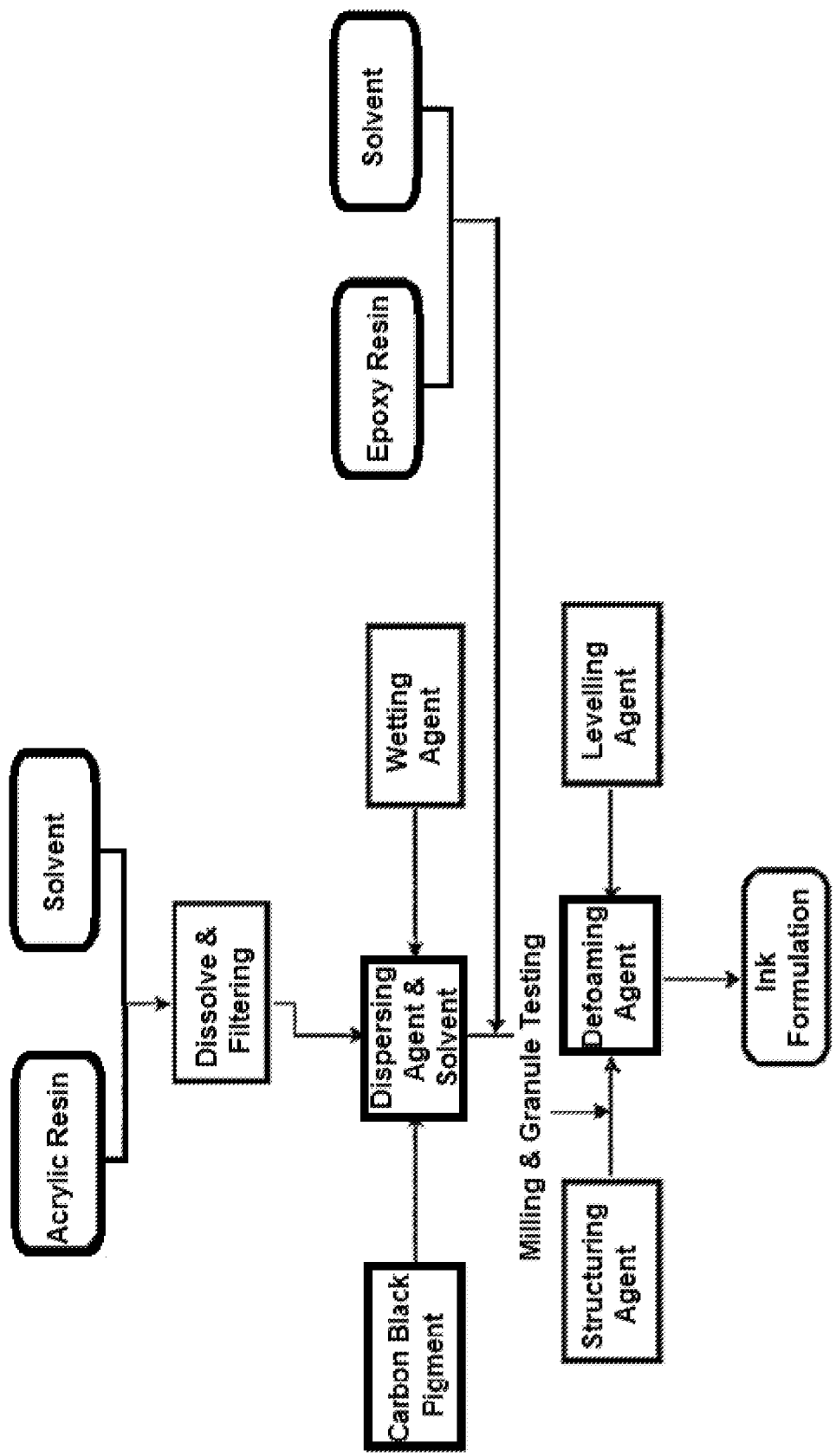
FIG. 5 shows an overview of the process for coating (masking) of the substrate.

The coating (masking material) can be made using techniques known to the person skilled in the art. An overview of the process is provided in FIG. 5.

The present invention makes use of conventional apparatus to accurately image arrayed molecules. Preferably, the coating is applied using screen print techniques known to the person skilled in the art. The substrates are screen printed to provide discrete reaction zones that are uncoated regions on the substrate.

Preferably the only areas of the substrate not coated are the discrete reaction zones. This makes it possible for robotic software to physically locate circular features and accurately deposit binding agents in a specific location. This is specifically important with increasing density of the discrete reaction zones which may increase the overall risk of rejections of the biochip based on the x and y coordinates of reaction zones.

The term microarray as used herein refers to a substrate that has a high density of discrete reaction zones. Accurate data can be obtained using up to approximately 1000 discrete reaction zones per 9 mm×9 mm area of substrate. Even at this high density of discrete reaction zones, high quality spots are produced having well defined borders. Advantages, such as improved accuracy of data, is also seen at lower density, such as substrates having 4 discrete reaction zones per 81 mm$^2$ area of substrate.

The substrate can be a large microarray substrate, for example approximately 100 mm×99 mm in size, wherein the substrate comprises square subsections, for example that are approximately 9 mm×9 mm in size, and wherein each square subsection comprises a grid of discrete reaction zones. The number of discrete reaction zones in each square subsection is in the range of from 2×2 to 30×30, preferably wherein each square section comprises a 5×5, 10×10, 20×20, or 30×30 grid of discrete reaction zones. Preferably, each discrete reaction zone is approximately 0.1 to 1 mm in diameter.

In a preferred embodiment, the coating of masking material is omitted from the edge of the 100 mm×99 mm substrate to create a non-coated border. Independent markers, such as square or elliptical patterns, are preferably fabricated at this uncoated edge region. This allows for calibration of a nano-dispenser to enable accurate identification of discrete reaction zones for accurate binding agents deposition within the reaction zones.

Preferably, the microarray has a density of discrete reaction zones in the range of from 0.08 to 15 zones/mm$^2$, more preferably 0.2 to 13 zones/mm$^2$, even more preferably 0.25 to 13 zones/mm$^2$. High quality data can be obtained even at these high densities.

Preferably the substrate has a thickness ranging from 0.5 to 5 mm, more preferably 0.5 to 3 mm, most preferably 0.5 to 1.5 mm and even more preferably the substrate has a thickness of about 0.5 mm.

Particularly preferred microarrays according to the invention have the following dimensions:

| Array type | Millimeter | | Array Density (Zones/mm$^2$) |
| --- | --- | --- | --- |
| | Circular Diameter | Pitch between circles | |
| 2 × 2 | 0.75 | 1.4 | 0.08 |
| 5 × 5 | 0.75 | 1.4 | 0.48 |

-continued

| Array type | Millimeter | | Array Density (Zones/mm$^2$) |
| --- | --- | --- | --- |
| | Circular Diameter | Pitch between circles | |
| 7 × 7 | 0.75 | 1.0 | 0.89 |
| 10 × 10 | 0.6 | 0.8 | 1.56 |
| 20 × 20 | 0.305 | 0.41 | 5.81 |
| 30 × 30 | 0.205 | 0.275 | 12.76 |

Preferably, the square subsections are breakable from each other. When manufacturing the substrates of the present invention, the starting substrate, made of glass, ceramic, plastic or silicon for example is laser scribed, preferably up to half the thickness of the substrate to allow for easy breakage.

In a preferred embodiment, the substrate comprises one or more binding agents immobilised on the surface, preferably immobilized on the discrete reaction zones.

The molecules immobilised to the substrate may be any suitable for use in an analyte assay. For example, the arrayed molecules may be polynucleotides, e.g., DNA, RNA or functional analogues thereof. Alternatively, proteins and peptides may be used, e.g., enzymes, antibodies, receptors or hormones. The molecules may also be viruses or an organic compound. The binding agents immobilized on the surface of the substrate may be any agent which can bind to the analytes of interest e.g. biomolecules, in particular antibodies, aptamers, phages and oligonucleotides, and non-biomolecules such as molecular imprinted polymers. Preferably the binding agents immobilised on the surface of the substrate are proteins. More preferably the binding agents are antibodies. The term "antibodies" refers to immunoglobulins which specifically recognises an epitope on a target as determined by the binding characteristics of the immunoglobulin variable domains of the heavy and light chains (VHS and VLS), more specifically the complementarity-determining regions (CDRs). Many potential antibody forms are known in the art, which may include, but are not limited to, a plurality of intact monoclonal antibodies or polyclonal mixtures comprising intact monoclonal antibodies, antibody fragments (for example Fab, Fab', and Fv fragments, linear antibodies single chain antibodies and multispecific antibodies comprising antibody fragments), single-chain variable fragments (scFvs), multi-specific antibodies, chimeric antibodies, humanised antibodies and fusion proteins comprising the domains necessary for the recognition of a given epitope on a target.

The skilled person will understand the conventional manufacturing steps that can be used to make the coated substrate according to the present invention. For example, the discrete reaction zones may be chemically activated to allow immobilisation of a binding agent. Preferably a chemical with reactive functional groups is added to the surface of the discrete reaction zones. The binding agent may be bound to the substrate via a linker. In particular, it is preferred that the surface is activated using an organosilane or polymer coating before reaction with the binding agent. The substrate of the present invention may be manufactured according to the method disclosed in, for example, GB-A-2324866 (EP0874242) the contents of which are incorporated herein in its entirety. It is of course desirable that the molecules retain maximum activity after the immobilisation procedure. Covalent immobilisation of the molecules may be carried out using conventional techniques, typically using a chemically reactive linker molecule, which can be activated under defined conditions. Preferably, the present invention uses surface modification technique based on plasma polymerisation, spin coating, CVD, wet coating and other coating methods. More preferably, the manufacturing method uses silanation for the immobilisation of binding agents. The chemical alteration may be performed before or after fabrication of the predefined discrete reaction zones. Preferably, the substrate is subjected to surface decontamination prior to activation or functionalization of the substrate.

The substrates of the present invention are demonstrated in the examples below. These examples are provided as an illustration only and should not be construed as limiting on the present invention.

Example 1

Ink based on Epoxy resin 25% w/w, e.g. Epon8111, Epon8021, Epikote 1004;
Carbon black pigment at 5% w/w, e.g. Elftex 285, Elftex 415, Elftex 435, Elftex 460;
Dispersing agent at 0.05% w/w, e.g. Disperbyk 190, Disperbyk 192, Disperbyk 168;
Acrylic resin at 5% w/w, e.g B-67, B-99N, DM-55,
Wetting agent at 0.2% w/w, e.g. SURFYNOL® 104BC, SURFYNOL® 104, SURFYNOL® 104DPM;
Structuring agent at 25% w/w, e.g. POLYWAX™ 3000; POLYWAX™ 400; CERAFLOUR® 965;
Defoaming agent at 1% w/w, e.g. BYK051, 055, 053;
Levelling agent at 3.75% w/w, e.g. BYK-358N; BYK-355; BYK-356;
Cross-linking agent at 5% w/w, e.g. Silquest A-2120; Silquest A-1110;
Solvent medium at 30% w/w, e.g. ethanol, propanol, xylene, diglycol, butyl ether.

Example 2

Ink based on Epoxy resin 22% w/w, e.g. Epon8021;
Carbon black pigment at 4% w/w, e.g. Elftex 460;
Dispersing agent at 0.05% w/w, e.g. Disperbyk 168;
Acrylic resin at 8% w/w, e.g DM-55;
Wetting agent at 0.2% w/w, e.g. SURFYNOL® 104BC;
Structuring agent at 20% w/w, e.g. POLYWAX™ 3000;
Defoaming agent at 0.85% w/w, e.g. BYK051;
Levelling agent at 3.9% w/w, e.g. BYK-358N;
Cross-linking agent 6% w/w, e.g. Silquest A-1110;
Solvent medium at 35% w/w, e.g. diglycol.

Example 3

Ink based on Epoxy resin 30% w/w, e.g. Epikote 1004;
Carbon black pigment at 5% w/w, e.g. Elftex 285;
Dispersing agent at 0.05% w/w, e.g. Disperbyk 190;
Acrylic resin at 10% w/w, e.g B-67;
Wetting agent at 0.2% w/w, e.g. SURFYNOL® 104BC;
Structuring agent at 20% w/w, e.g. CERAFLOUR® 965;
Defoaming agent at 1% w/w, e.g. BYK055;
Levelling agent at 1% w/w, e.g. BYK-355;
Cross-linking agent at 2.75% w/w, e.g. Silquest A-1110;
Solvent medium at 30% w/w, e.g. butyl ether.

Example 4

Raw ceramic sheet based on aluminium oxide containing a polished top surface and unpolished bottom surface was laser scribed on the bottom surface up to half the thickness of the ceramic sheet to allow easy breakage during biochip assembly. The ceramic sheet was subjected to surface decontamination using surfactant water mixture and microwave plasma treatment using 1:1 mixture of Ar and $O_2$ for 10 mins. The surface was chemically activated by wet silanation coating technique followed by thermal curing at 140° C. for 2 hours.

The chemically functionalised surface was loaded on to a screen printer. An emulsion screen containing the desired microarray pattern was loaded on the printer with an ink selected from examples 1 to 3 above. The design pattern was transferred to the sheet using squeegee.

Continuous screen printing of the substrate was achieved through repetitive action of squeeze and flood blade that spreads ink again on the screen. Freshly printed sheets were thermally cured at 140° C. for 20 minutes achieving dry print thickness of 10-20 μm.

Screen printed ceramic sheets were then loaded on to a nano-dispenser used for biomolecule deposition. Accurate identification of the chemically activated discrete reaction zones was achieved by an internal calibration mark present on the ceramic sheet. The nano-dispenser was used to generate arrays of 5×5 up to 30×30 based on the selected print design.

The following circular diameter range and designs were made:

| Array type | Millimeter | | Array Density (Zones/mm$^2$) |
|---|---|---|---|
| | Circular Diameter | Pitch between circles | |
| 2 × 2 | 0.75 | 1.4 | 0.08 |
| 5 × 5 | 0.75 | 1.4 | 0.48 |
| 7 × 7 | 0.75 | 1.0 | 0.89 |
| 10 × 10 | 0.6 | 0.8 | 1.56 |
| 20 × 20 | 0.305 | 0.41 | 5.81 |
| 30 × 30 | 0.205 | 0.275 | 12.76 |

Figures 2A, 2B:
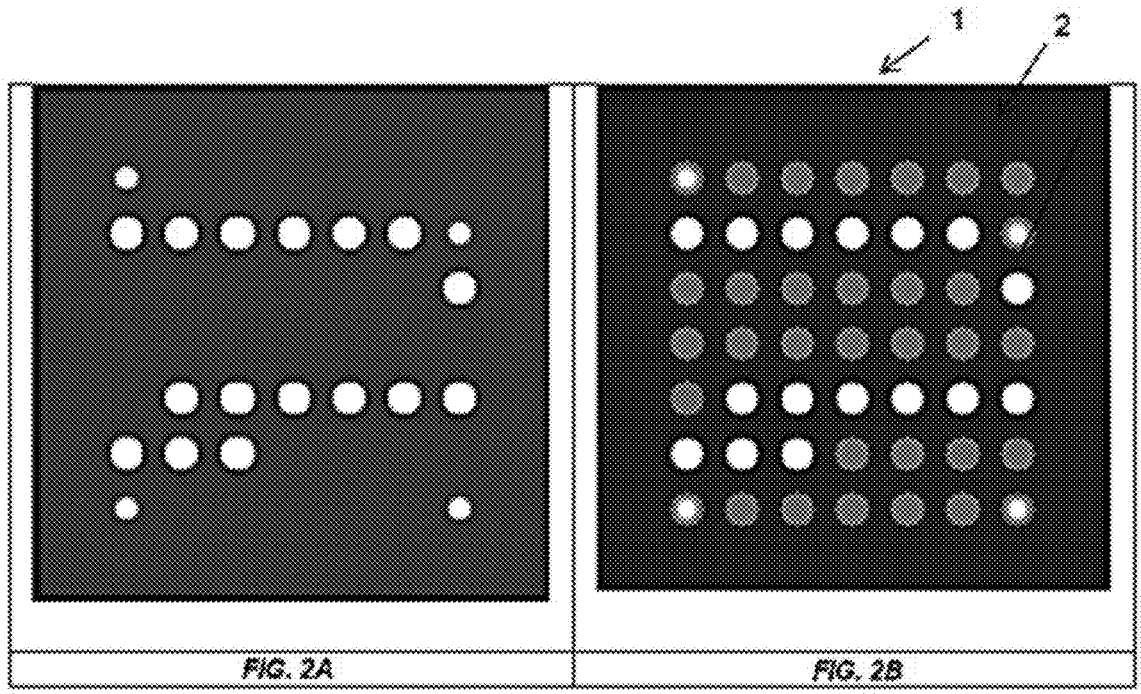
FIG. 2A-B shows images of reference spots in 7×7 array format.
Figures 3A, 3B:
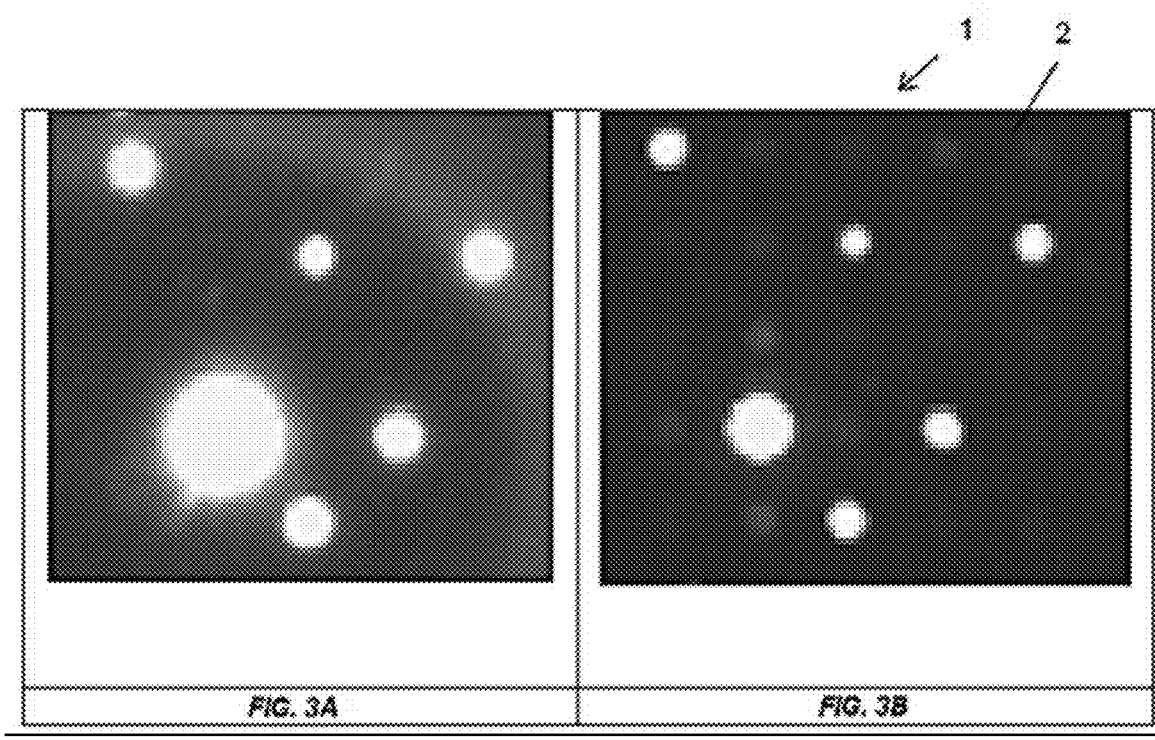
FIG. 3A-B shows an image of a thyroid free array containing reference spots, FT4 (free Thyroxine), FT3 (triiodothyronine) and TSH (Thyroid Stimulating Hormone) capture antibody. Where FT4 and FT3 are competitive assay and TSH is sandwich assay.
Figure 4:
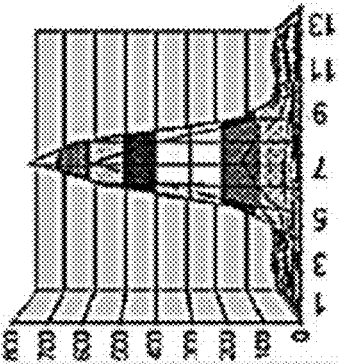
FIG. 4 shows the improvement in detection sensitivity of a microarray according to the present invention compared to control. This image shows TSH (Thyroid Stimulating Hormone) assay for determination of lower levels of sensitivity. The first column shows expected sensitivity, the 2nd and 5th column shows measured sensitivity on uncoated and coated substrate, respectively. The 3rd and 6th column shows typical 3D pixel plot acquired by digital sensor. The 4th and 7th column show improvement in signal to noise ratio.
Figure 4:
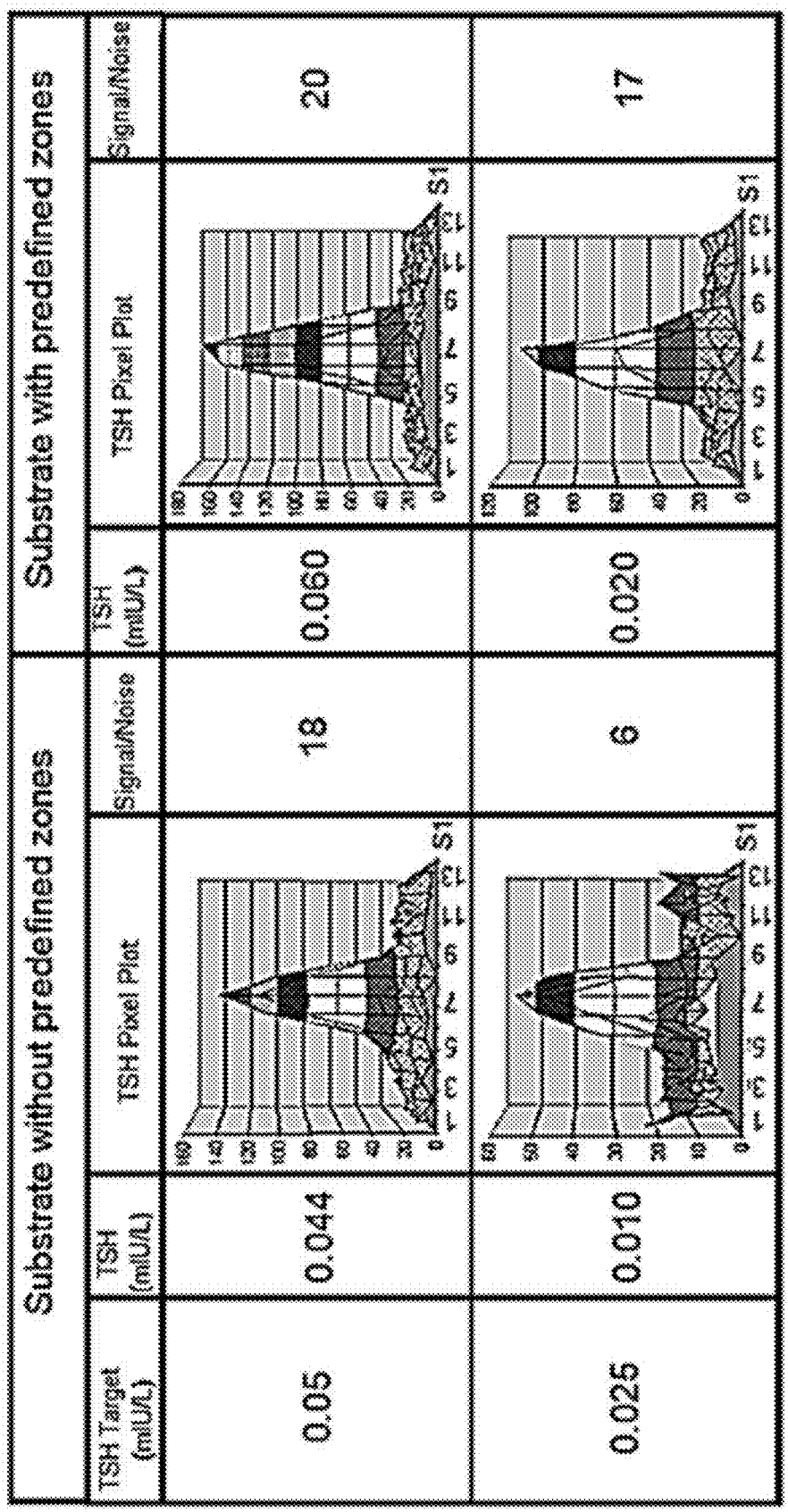

The microarrays were dried at room temperature for 2 hrs, followed by blocking and stabilising. The microarrays were cut and assembled in carrier wells for running diagnostic tests on Randox analysers. Improved data is visualised through digital sensor using chemiluminescent technique. FIGS. 2, 3 and 4 show the images and data collected from these examples. FIG. 2 shows a 7×7 array of reference spot according to the invention, FIG. 3 shows a 5×5 array (Thyroid Free) according to the invention and FIG. 4 shows a 5×5 array (Thyroid Free) according to the invention.

The invention claimed is:

1. A substrate comprising a thermally cured coating of a masking material, and a plurality of discrete reaction zones onto which one or more binding agents are intended to be attached, wherein said zones are uncoated areas on the substrate, wherein the masking material and has a contact angle of 60-120° and comprises a pigment, an acrylic resin, and a structuring agent, wherein the structuring agent is PTFE wax.

2. A substrate according to claim 1, wherein the coating has been thermally cured at a temperature of at least 140° C.

3. A substrate according to claim 1, wherein the substrate is approximately 100 mm×99 mm in size, and wherein the substrate comprises square subsections that are approximately 9 mm×9 mm in size, each square subsection comprising a grid of discrete reaction zones, and wherein each square subsection comprises a grid of from 5×5, 10×10, 20×20, or 30×30 discrete reaction zones.

4. A substrate according to claim 1, wherein the density of the discrete reaction zones is in the range of from 0.08 to 15 zones/mm².

5. A substrate according to claim 1, wherein each discrete reaction zone has a diameter ranging from 0.1 mm to 1 mm in diameter.

6. A substrate according to claim 1 comprising one or more binding agents immobilised on the discrete reaction zones.

7. A substrate according to claim 1, wherein the substrate comprises silicon, metal oxides, glass or plastic.

8. A substrate according to claim 1, wherein the contact angle is 90°-120°.

9. A substrate according to claim 1, wherein the thickness of the coating applied to the substrate is 2 to 50 μm (micron) thick.

10. A substrate according to claim 1, wherein the coating of masking material is a colour ranging from off-white to black.

11. A substrate according to claim 1, wherein the discrete reaction zones are chemically activated to allow immobilization of binding agent.

12. A substrate according to claim 1, wherein the masking material comprises an epoxy resin.

13. A substrate according to claim 1, wherein:
the pigment is present in an amount of 1 to 8% w/w of the masking composition;
the epoxy resin is present in an amount of 15 to 50% w/w of the masking composition,
the acrylic resin is present in an amount of 2 to 10% w/w of the masking composition, and
the structuring agent is present in an amount of 15 to 50% w/w of the masking composition.

14. A substrate according to claim 1, wherein
the pigment is present in an amount of about 5% w/w of the masking composition;
the epoxy resin is present in an amount of about 30% w/w of the masking composition,
the acrylic resin is present in an amount of about 10% w/w of the masking composition, and
the structuring agent is present in an amount of about 20% w/w of the masking composition.

15. A substrate according to claim 1, wherein the binding agents are antibodies.

16. A substrate according to claim 1, wherein the masking material does not contain silicon.

17. A substrate according to claim 4, wherein the density of the discrete reaction zones is in the range of from 0.2 to 13 zones/mm³.

18. A substrate according to claim 7, wherein the substrate is glass.

19. A substrate according to claim 13, wherein the pigment is a black pigment.

20. A method of forming a substrate according to claim 1, the method comprising:
(a) forming a plurality of discrete reaction zones on the surface of the substrate;
(b) applying the masking material to the surface of the substrate other than the plurality of discrete reaction zones; and
(c) thermally curing the masking material to form a coating of the masking material on the surface of the substrate.

21. A method according to claim 20, wherein the masking material is thermally cured at a temperature of at least 140° C.

22. A method according to claim 20, wherein the masking material is applied by screen printing.

* * * * *